(12) United States Patent
Onodera

(10) Patent No.: US 8,018,484 B2
(45) Date of Patent: Sep. 13, 2011

(54) FEELING AND PHYSICAL CONDITION STABILIZER FOR STABILIZING USER'S FEELING AND PHYSICAL CONDITION

(75) Inventor: Takashi Onodera, Tokyo (JP)

(73) Assignee: Universal Entertainment Corporation, Tokyo (JP)

( * ) Notice: Subject to any disclaimer, the term of this patent is extended or adjusted under 35 U.S.C. 154(b) by 1366 days.

(21) Appl. No.: 11/550,133

(22) Filed: Oct. 17, 2006

(65) Prior Publication Data

US 2007/0098349 A1    May 3, 2007

(30) Foreign Application Priority Data

Oct. 21, 2005   (JP) .................................. 2005-307896

(51) Int. Cl.
*H04N 9/47* (2006.01)
*G01S 15/89* (2006.01)
(52) U.S. Cl. .......................................... 348/61; 348/163
(58) Field of Classification Search .................... 348/61, 348/143

See application file for complete search history.

(56) References Cited

U.S. PATENT DOCUMENTS

| | | | |
|---|---|---|---|
| 2002/0022551 A1* | 2/2002 | Watterson et al. | 482/8 |
| 2004/0113793 A1* | 6/2004 | Braxton | 340/573.1 |
| 2006/0126444 A1* | 6/2006 | Ellner et al. | 368/246 |
| 2009/0253554 A1* | 10/2009 | McIntosh | 482/4 |

FOREIGN PATENT DOCUMENTS

JP   2002-366276   12/2002

* cited by examiner

*Primary Examiner* — Jerry Dennison
(74) *Attorney, Agent, or Firm* — Oblon, Spivak, McClelland, Maier & Neustadt, L.L.P.

(57) ABSTRACT

An information processing unit is provided which positively stabilizes a user's feeling and physical condition by deciding the user's feeling and physical condition based on the user's body temperature change and the like. Depending on the user's hand temperature, a CPU (110) automatically selects an aromatic for stabilizing the user's feeling and physical condition change, and directs an aromatic sprayer (50) to spray the aromatic, or directs a display part (40) to display a countermeasure message for maintaining the physical condition. This positively stabilizes the user's feeling and physical condition.

9 Claims, 18 Drawing Sheets

(SPRAY TIME AND SPRAY INTERVAL DECISION PROCESS)

FIG. 15

FEELING AND PHYSICAL CONDITION DECISION TABLE

| THRESHOLD VALUE | PHYSICAL CONDITION DECISION |
|---|---|
| TEMPERATURE SIGNAL INCREMENT IS 0.5°C OR MORE | EXCITATION |
| TEMPERATURE SIGNAL DECREMENT IS 0.5°C OR MORE | TENSION |
| TEMPERATURE SIGNAL VARIATION OF LESS THAN ±0.5°C LASTING 5 MIN OR MORE | NORMAL |
| ⋮ | ⋮ |

FIG. 16

AROMATIC SELECTING TABLE BASED ON PHYSICAL CONDITION DECISION

| PHYSICAL CONDITION | AROMATIC |
|---|---|
| EXCITATION | LAVENDER |
| TENSION | CATECHIN |
| ⋮ | ⋮ |

FIG. 17

SPRAY TIME SELECTING TABLE BASED
ON PHYSICAL CONDITION DECISION

| PHYSICAL CONDITION | TIME | INTERVAL |
|---|---|---|
| EXCITATION | 10 MIN | 15 MIN |
| TENSION | 2 MIN | 5 MIN |
| ⋮ | ⋮ | ⋮ |

FIG. 18

MESSAGE SELECTING TABLE BASED ON
PHYSICAL CONDITION DECISION

| PHYSICAL CONDITION | MESSAGE |
|---|---|
| HUNGER | HOW ABOUT TAKING A MEAL? |
| FATIGUE | HOW ABOUT TAKING A BREAK? |
| ⋮ | ⋮ |

FIG. 19

AROMATIC AND SPRAY TIME SELECTING TABLE BASED ON SENSOR OUTPUT VALUES

| THRESHOLD VALUE | AROMATIC | TIME | INTERVAL |
|---|---|---|---|
| TEMPERATURE SIGNAL INCREMENT IS 0.5°C | LAVENDER | 10 MIN | 15 MIN |
| TEMPERATURE SIGNAL DECREMENT IS 0.5°C | CATECHIN | 2 MIN | 5 MIN |
| ⋮ | ⋮ | ⋮ | ⋮ |

FIG. 20

MESSAGE SELECTING TABLE BASED ON SENSOR OUTPUT VALUES

| THRESHOLD VALUE | MESSAGE |
|---|---|
| TEMPERATURE SIGNAL INCREMENT IS 0.5°C | HOW ABOUT TAKING A BREAK? |
| TEMPERATURE SIGNAL DECREMENT IS 0.5°C | DO DEEP BREATHING AND CALM DOWN |
| ⋮ | ⋮ |

FIG. 21

SELECT DATA FILE NAME

1. Tanaka2005/06/15

2. Satou2005/08/31

2. Suzuki2005/10/01

FIG. 22

SELECT AROMATIC

TANK A  MINT

TANK B  ORANGE

TANK C  LAVENDER

SELECTION

A+B

FEELING AND PHYSICAL CONDITION STABILIZER FOR STABILIZING USER'S FEELING AND PHYSICAL CONDITION

This application is based on and claims the benefit of priority from Japanese Patent Applications No. 2005-307896, filed on Oct. 21, 2005 the contents of which are incorporated herein by reference.

BACKGROUND OF THE INVENTION

1. Field of the Invention

The present invention relates to a feeling and physical condition stabilizer for stabilizing a user's feeling and physical condition.

2. Related Art

Conventionally, there have been proposed information processing units including means for detecting a change in the user's body temperature, which incorporate a temperature sensor in an input unit such as a keyboard.

For example, Japanese Patent Unexamined Publication No. 2002-366276 discloses an empathy type word processor that captures a user's feeling change based on the user's body temperature change sensed by a temperature sensor, and outputs an appropriate sentence based on the feeling change.

SUMMARY OF THE INVENTION

However, there has not yet been provided any means which positively stabilizes feeling and physical condition by deciding the user's feeling and physical condition based on the user's body temperature change and the like.

To this end, the present invention aims at providing an information processing unit for stabilizing a user's feeling and physical condition. Particularly, the present invention provides the following.

According to a first aspect of the present invention, an information processing unit includes: (i) an input part with a temperature sensor which accepts an input operation of a user and, in response to a contact of the user's hand at the time of the input, measures the temperature of the hand; (ii) a container for holding an aromatic; (iii) an aromatic spray part having a passage communicating with the container and a nozzle communicating with the passage; and (iv) an aromatic spray controller that is connected via an interface to the temperature sensor and controls the aromatic spray part, based on a temperature signal from the temperature sensor. The aromatic spray controller receives a temperature signal from the temperature sensor and, when a temperature indicated by the temperature signal reaches a predetermined temperature, outputs to the aromatic spray part an aromatic spray start signal directing it to spray an aromatic from the nozzle of the aromatic spray part.

This information processing unit measures the temperature of the user's hand in response to a contact of the hand, and sprays an aromatic in the mist state, depending on the determination of the user's hand temperature.

According to a second aspect of the present invention, as described in the information processing unit of the first aspect, (i) the container of the aromatic spray part is constructed so that a plurality of different kinds of aromatics can be held; (ii) a plurality of nozzles is provided so that different aromatics can be sprayed, and (iii) the aromatic spray controller, depending on the temperature signal from the temperature sensor, outputs to the aromatic spray part an aromatic spray start signal directing it to spray a suitable kind of aromatic.

This information processing unit has a plurality of different kinds of aromatics and, depending on the determination of the user's finger temperature, selects a suitable one from the plurality of different aromatics and then sprays it in a mist state.

According to a third aspect of the present invention, as described in the information processing unit of the first aspect, the aromatic spray part is provided outside a main body of the information processing unit.

The aromatic spray part is provided at the outside of the main body of the information processing unit.

According to a fourth aspect of the present invention, as described in the information processing unit of the first aspect, the input part is a mouse or a keyboard.

In this information processing unit, the mouse or the keyboard has a temperature sensor.

According to a fifth aspect of the present invention, as described in the information processing unit of the first aspect, the nozzle of the aromatic spray part is provided on either the inside of the main body of the information processing unit or the inside of the input part, or alternatively, either the outside of the main body of the information processing unit or the outside of the input part.

According to a sixth aspect of the present invention, an information processing unit includes: (i) an input part with a temperature sensor which accepts an input operation of a user and, in response to a contact of the user's hand at the time of the input, measures a temperature of the hand; and (ii) a controller housed in a main body and connected via an interface to the temperature sensor, the controller responding to a temperature signal from the temperature sensor and, when a temperature indicated by the temperature signal reaches a predetermined temperature, reading from a storage part countermeasure message data indicating a countermeasure message previously stored in the storage part, and then sending to a display part a display signal directing it to display the countermeasure message.

This information processing unit is adapted to display the countermeasure message on the display part, depending on the user's hand temperature.

According to a seventh aspect of the present invention as described in the information processing unit of the sixth aspect, the input part is a mouse or a keyboard.

According to an eighth aspect of the present invention, a game machine includes: (i) an input part with a temperature sensor which accepts an input operation of a user and, in response to a contact of the user's hand at the time of the input, measures the temperature of the hand; (ii) a container for holding an aromatic; (iii) an aromatic spray part having a passage communicating with the container and a nozzle communicating with the passage; and (iv) an aromatic spray controller that is connected via an interface to the temperature sensor and controls the aromatic spray part, depending on a temperature signal from the temperature sensor. The aromatic spray controller receives a temperature signal from the temperature sensor and, when a temperature indicated by the temperature signal reaches a predetermined temperature, outputs to the aromatic spray part an aromatic spray start signal directing it to spray an aromatic from the nozzle of the aromatic spray part.

The game machine is adapted to measure the temperature of the user's hand in response to a contact of the hand, and sprays an aromatic in the mist state, depending on the determination of the user's hand temperature.

According to a ninth aspect of the present invention as described in the game machine of the eighth aspect, (i) a container of the aromatic spray part is constructed so that a plurality of different kinds of aromatics can be held, (ii) a plurality of nozzles is provided so that different aromatics can be sprayed, and (iii) the aromatic spray controller, depending on the temperature signal from the temperature sensor, outputs to the aromatic spray part an aromatic spray start signal directing it to spray a suitable kind of aromatic.

According to a tenth aspect of the present invention as described in the game machine of the eighth aspect, the aromatic spray part is provided at the outside of a main body of the game machine.

According to an eleventh aspect of the present invention as described in the game machine of the eighth aspect, the nozzle of the aromatic spray part is provided on either the inside of the main body of the game machine or the inside of the input part, or alternatively, either the outside of the main body of the game machine or the outside of the input part.

According to a twelfth aspect of the present invention, a game machine includes: (i) an input part with a temperature sensor which accepts an input operation of a user and, in response to a contact of the user's hand at the time of the input, measures the temperature of the hand; and (ii) a controller housed in a main body and connected via an interface to the temperature sensor, the controller responding to a temperature signal from the temperature sensor and, when a temperature indicated by the temperature signal reaches a predetermined temperature, reading from a storage part counter message data indicating a countermeasure message previously stored in the storage part, and then sending to a display part a display signal directing it to display the countermeasure message.

BRIEF DESCRIPTION OF THE DRAWINGS

FIG. 15 shows a feeling and physical condition decision table 70 of the information processing unit 1 in an example of the preferred embodiment;

FIG. 16 shows an aromatic selection table 74 based on the physical condition decision made by the information processing unit 1 in an example of the preferred embodiment;

FIG. 17 shows a spray time selection table 74 based on the physical condition decision made by the information processing unit 1 in the preferred embodiment;

FIG. 18 shows a message selection table 76 based on the physical condition decision made by the information processing unit 1 in an example of the preferred embodiment;

FIG. 19 shows an aromatic and spray time selection table 80 based on sensor output values in the information processing unit 1 in an example of the preferred embodiment;

FIG. 20 shows a message selection table 82 based on the sensor output values in the information processing unit 1 in an example of the preferred embodiment;

FIG. 21 shows an example of display during a custom table selecting process in the information processing unit 1 in an example of the preferred embodiment;

FIG. 22 shows a display during an aromatic selecting process in the information processing unit 1 in an example of the preferred embodiment;

DETAILED DESCRIPTION OF THE INVENTION

Preferred embodiments of the present invention will be described below with reference to the accompanying drawings.

Figure 1:
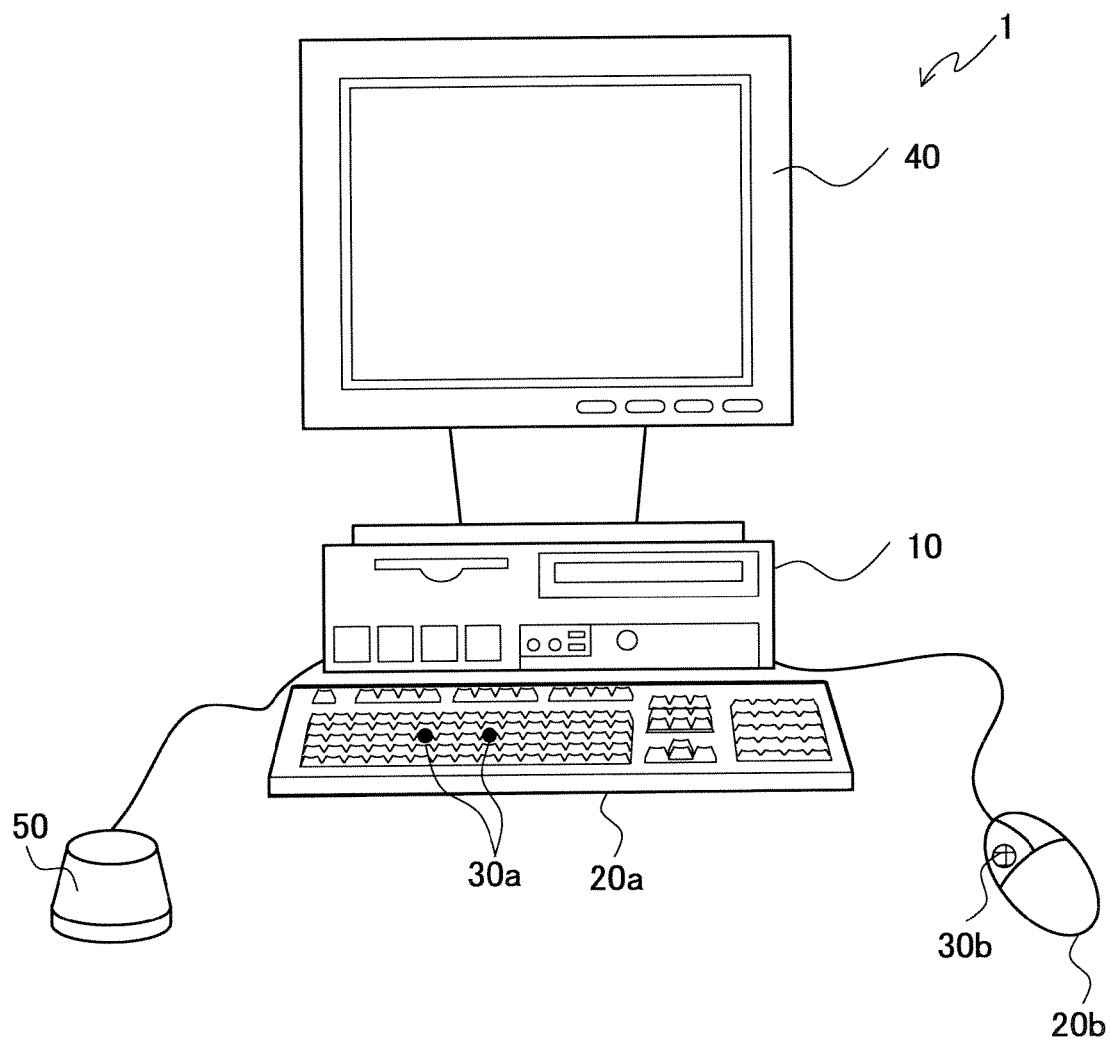
FIG. 1 illustrates a physical schematic configuration of an information processing unit 1 according to an example of a preferred embodiment of the present invention.

FIG. 1 illustrates a case where an information processing unit 1 according to a preferred embodiment of the present invention is configured as a desktop personal computer (PC). The information processing unit 1 is constructed of an aromatic sprayer 50, input parts 20a and 20b containing temperature sensing parts 30a and 30b, respectively, a display part 40, and a main body 10. The number of the temperature sensing parts 30a and 30b is not limited to the number shown in this embodiment.

Figure 2:
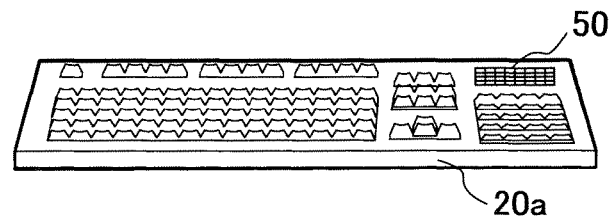
FIGS. 2 to 4 illustrate examples of the arrangement of an aromatic sprayer 50 of the information processing unit 1 in the preferred embodiment.
Figure 3:
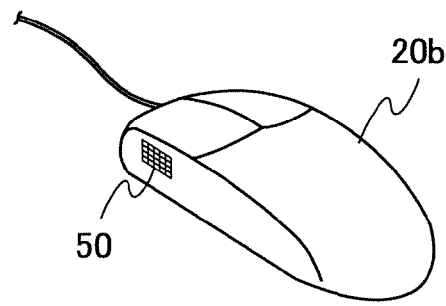
Figure 4:
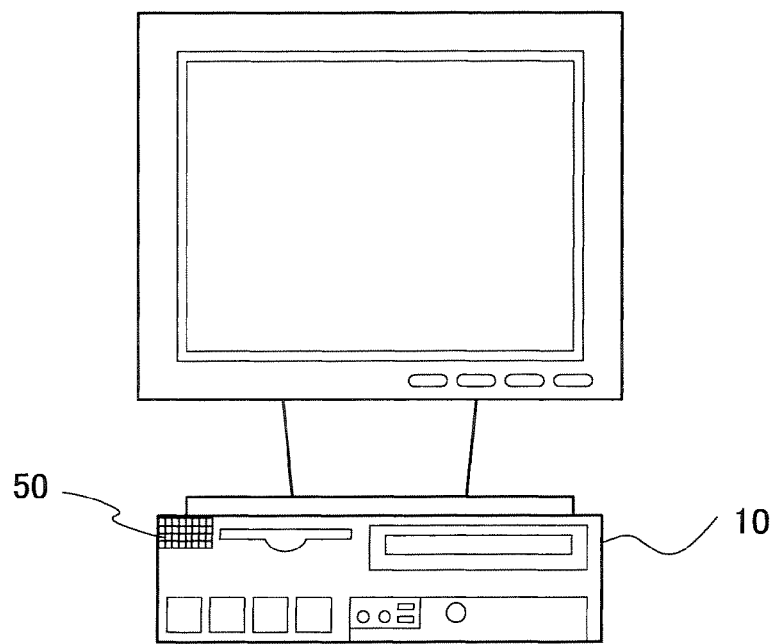

The aromatic sprayer 50 can be provided on the outside of the main body 10, or the outside of the input parts 20a and 20b, as shown in FIG. 1. As an alternative, the aromatic sprayer 50 may be placed on (housed in) the inside of the input parts 20a and 20b. Examples of an arrangement of the aromatic sprayer 50 in this case are shown in FIGS. 2 and 3. In another alternative, the aromatic sprayer 50 may be placed at (housed in) the inside of the main body 10. An example of arrangement of the aromatic sprayer 50 in this case is shown in FIG. 4.

The information processing unit 1 may be configured as an information processing unit constantly accepting inputs from the user, such as a notebook-sized PC, a PDA, or a game machine, besides the above-mentioned desktop PC.

Thus, the aromatic sprayer 50 may be located at the front face or the side face of the display part 40 or the main body 10 or the input parts 20a, 20b in various types of the above-mentioned information processing units 1.

The input parts 20a and 20b may be formed of a region that is subject to frequent contact with the user's finger skin or palm skin, or a region that supports the former region, that accepts input from the user, namely a pointing device such as a mouse, a touch pad, or a joy stick.

Preferably, the temperature sensing parts 30a and 30b are provided at portions that are located on the surfaces of the input parts 20a and 20b of the information processing unit 1, and that are subject to frequent contact with the user's finger or palm skin, in order to measure the user's body temperature more suitably.

Figure 5:
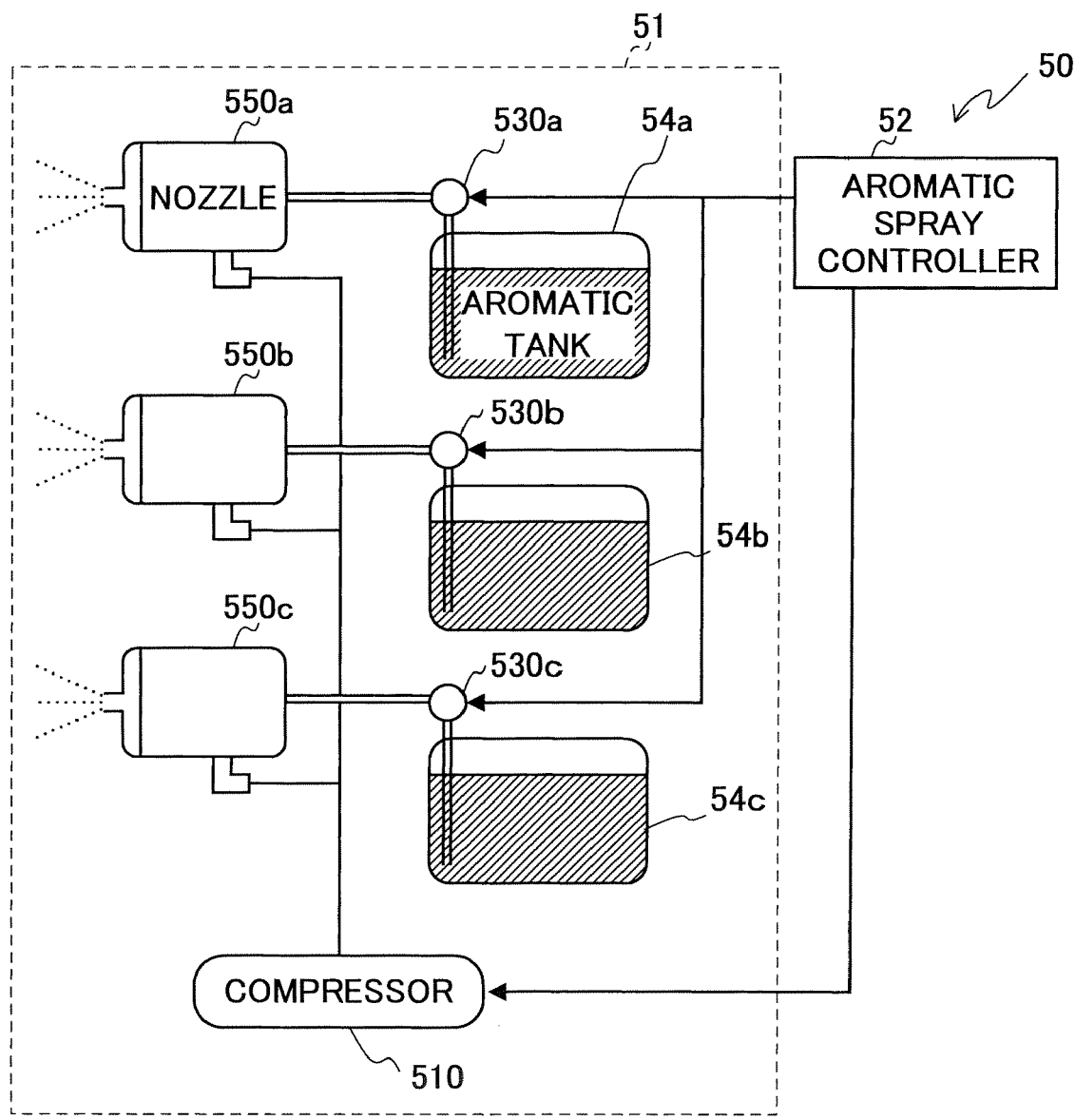
FIG. 5 illustrates a schematic configuration of the aromatic sprayer 50 of the information processing unit 1 in an example of the preferred embodiment.

FIG. 5 illustrates an example of the configuration of the aromatic sprayer 50 in the information processing unit 1. The aromatic sprayer 50 has an aromatic spray part 51 and an aromatic spray controller 52. The aromatic spray part 51 has aromatic tanks 54a, 54b and 54c as containers of aromatics, aromatic tank pumps 530a, 530b and 530c, a compressor 510, and nozzles 550a, 550b and 550c.

The aromatic tanks 54a, 54b and 54c, which can hold a plurality of aromatics, and the nozzles 550a, 550b and 550c are connected to one another via passages and the aromatic tank pumps 530a, 530b and 530c, respectively.

The aromatic spray controller 52 controls the aromatic tank pumps 530a, 530b and 530c, the compressor 510, and the nozzles 550a, 550b and 550c. Based on temperature signals to be received from the temperature sensing parts 30a and 30b, the aromatic spray controller 52 selects one or a plurality of aromatics, and outputs an aromatic spray start signal for directing the nozzles to spray the aromatic from the corresponding nozzle.

Although the nozzles 550a, 550b and 550c are provided so as to correspond to the number of aromatics, a common nozzle may be used. In this case, the passages communicating to the aromatic tanks 54a, 54b and 54c are communicated to a single nozzle, and a mixed solution of a plurality of aromatics is sprayed from this nozzle.

Alternatively, the aromatic tanks 54a, 54b and 54c may be integrally molded and configured as a single aromatic tank partitioned by diaphragms into three regions. Alternatively, the number of the aromatic tanks and the number of partitions may be set arbitrarily.

Figure 6:
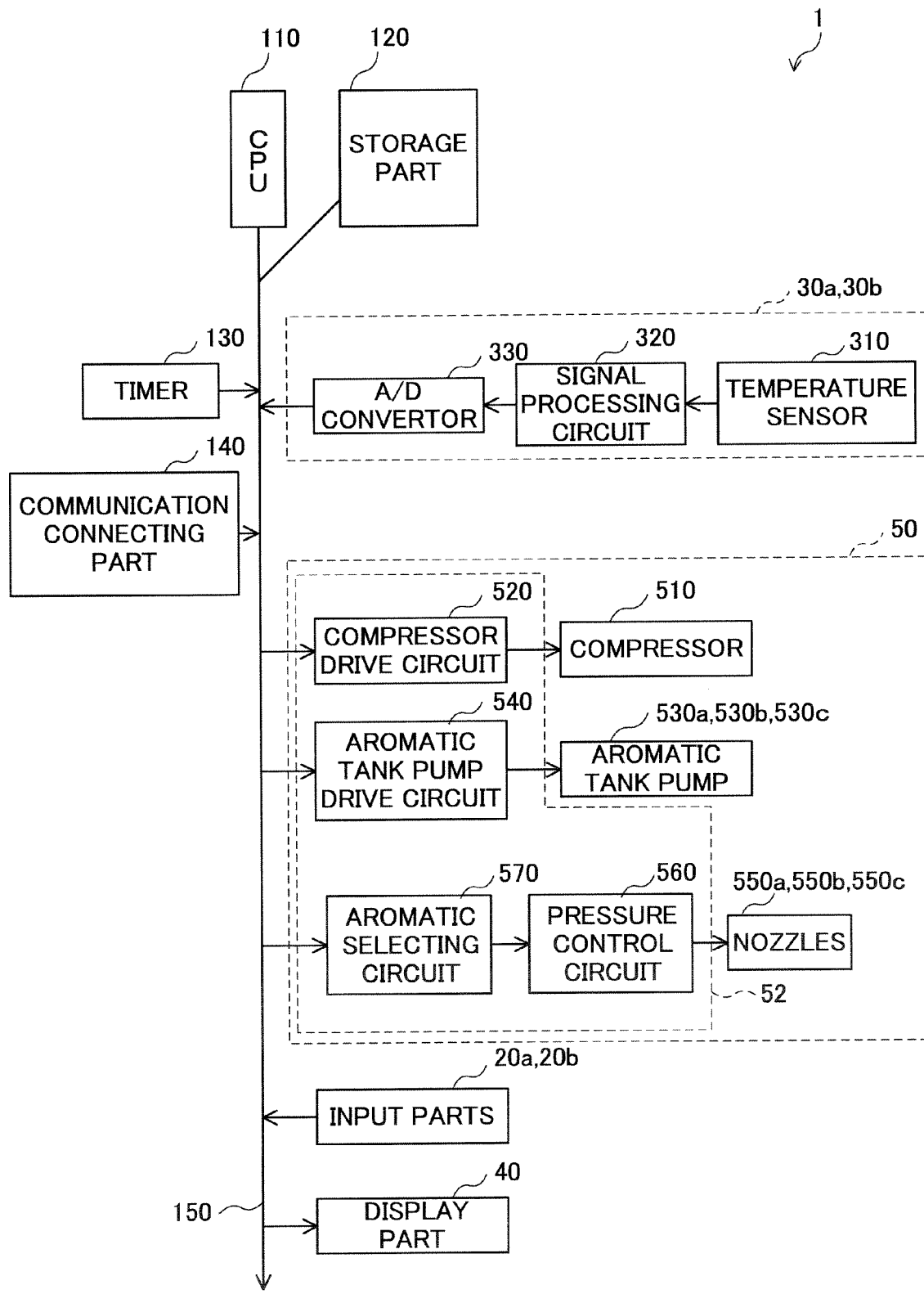
FIG. 6 is a block diagram illustrating the electrical schematic configuration of the information processing unit 1 in an example of the preferred embodiment.

FIG. 6 illustrates a circuit configuration containing the CPU 110 controlling the aromatic spray operation of the information processing unit 1, and peripheral devices electrically connected to the CPU 110, according to an example of the preferred embodiment of the present invention.

Main peripheral devices whose operations are controlled by the CPU 110 with the use of their respective corresponding control signals are a storage part 120, the aromatic sprayer 50, and the display part 40.

Main input signal generating means that generate input signals necessary for the CPU 110 to issue control commands are the temperature sensing parts 30a, 30b, the input parts 20a, 20b, and the timer 130.

These control signals and input signals are transmitted via a transmission path 150 to the corresponding parts. The CPU 110 communicates with the exterior of the information processing unit 1 via a communication connecting part 140.

Thus, the CPU 110 reads and executes a program stored in the storage part 120 so as to cooperate with the above-mentioned hardware (the peripheral devices) to implement various means related to the present invention.

The storage part 120 stores various control commands, and a group of various tables used in a series of spray operations which will be described later in detail, as well as aromatic data during spraying, spray start time, and the like.

The aromatic spray controller 52 is provided with a compressor drive circuit 520 that drives and controls the compressor 510, an aromatic tank pump drive circuit 540 that drives and controls the aromatic tank pumps 530a, 530b and 530c, a pressure control circuit 560 for press-outputting aromatics from the nozzles 550a, 550b and 550c, and an aromatic selecting circuit 570. The aromatic spray controller 52 is connected via the transmission path 150 to the CPU 110. Upon receipt of a control signal outputted from the CPU 110, such as a drive command, the aromatic spray controller 52 controls the operations of the respective circuits.

The temperature sensing parts 30a and 30b are constructed of a temperature sensor 310, a signal processing circuit 320, and an A/D converter 330. A temperature signal from the temperature sensor 310 is converted to a digital signal by the A/D converter 330 via the signal processing circuit 320, and then stored in the storage part 120.

The value of a temperature signal from the temperature sensor 310 varies to a greater extent than normal, with variations in the user's feelings and physical conditions such as excitation and tension. Although the details will be described later, the CPU 110 receives the digitalized temperature signal and monitors its fluctuation range, in order to decide the user's feeling and physical condition, or to select an aromatic effective in relaxing the user's feelings and physical conditions, or to select a countermeasure message and the like for relaxing the user's feelings and physical conditions.

As an alternative, the temperature sensor 310 may be replaced with a pulse sensor (not shown) that measures the user's pulse through contact with the finger, and converts and sends it as an electrical signal. In the following, the information processing unit 1 may also be configured by reading the term "temperature" as "pulse." The location of the pulse sensor is similar to that of the temperature sensor 310. Instead of the temperature fluctuation range, the pulse fluctuation range is used to decide the feeling and physical condition, or an aromatic or a countermeasure message. Alternatively, the temperature sensor 310 and the pulse sensor may be provided together so that the input values from both sensors are combined to select the feeling and physical condition, or an aromatic or a countermeasure message.

Main Flow A

Figure 7:
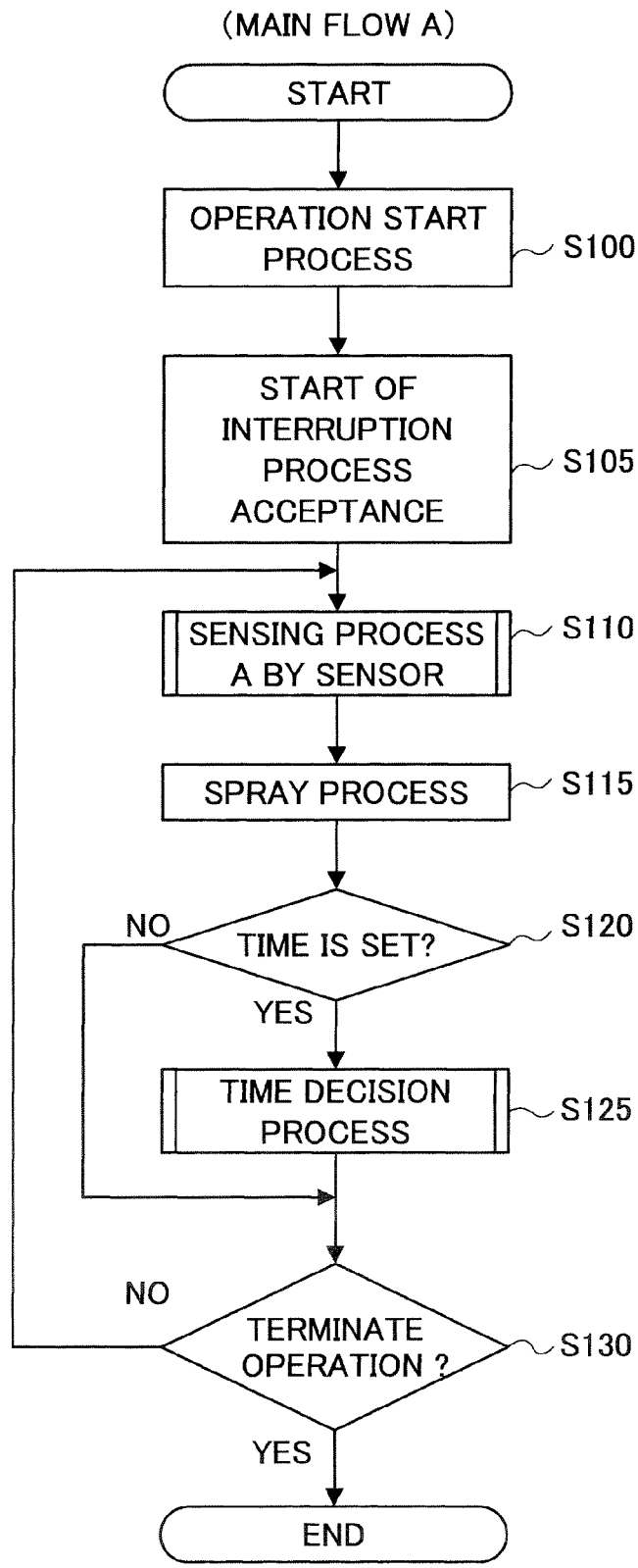
FIGS. 7 to 14 are flow charts illustrating process flow in the information processing unit 1 in an example of the preferred embodiment.

FIG. 7 is a main flow chart illustrating the spray process of the information processing unit 1. The main process of the spray process will be described below.

In step S100, the input of the power of the information processing unit 1 triggers the start of operation of the CPU 110 and the peripheral devices. Alternatively, a dedicated power switch to start the operation of the CPU 110 and the peripheral devices may be prepared.

Also in step S100, the CPU 110 reads a set of setting tables to be used in the succeeding process. The set of setting tables has configurations as shown in tables 70, 72, 74, 76, 80, and 82 in FIGS. 15 to 20, and stores predefined data or data retained at the time of the previous operation. A plurality of sets of setting tables can be managed, and the data set per user can be retained as a custom table. Specifically, the plurality of sets can be replaced and used in a custom table reading process (FIG. 10) to be described later. When this process is terminated, the procedure moves to step S105.

Figure 9:
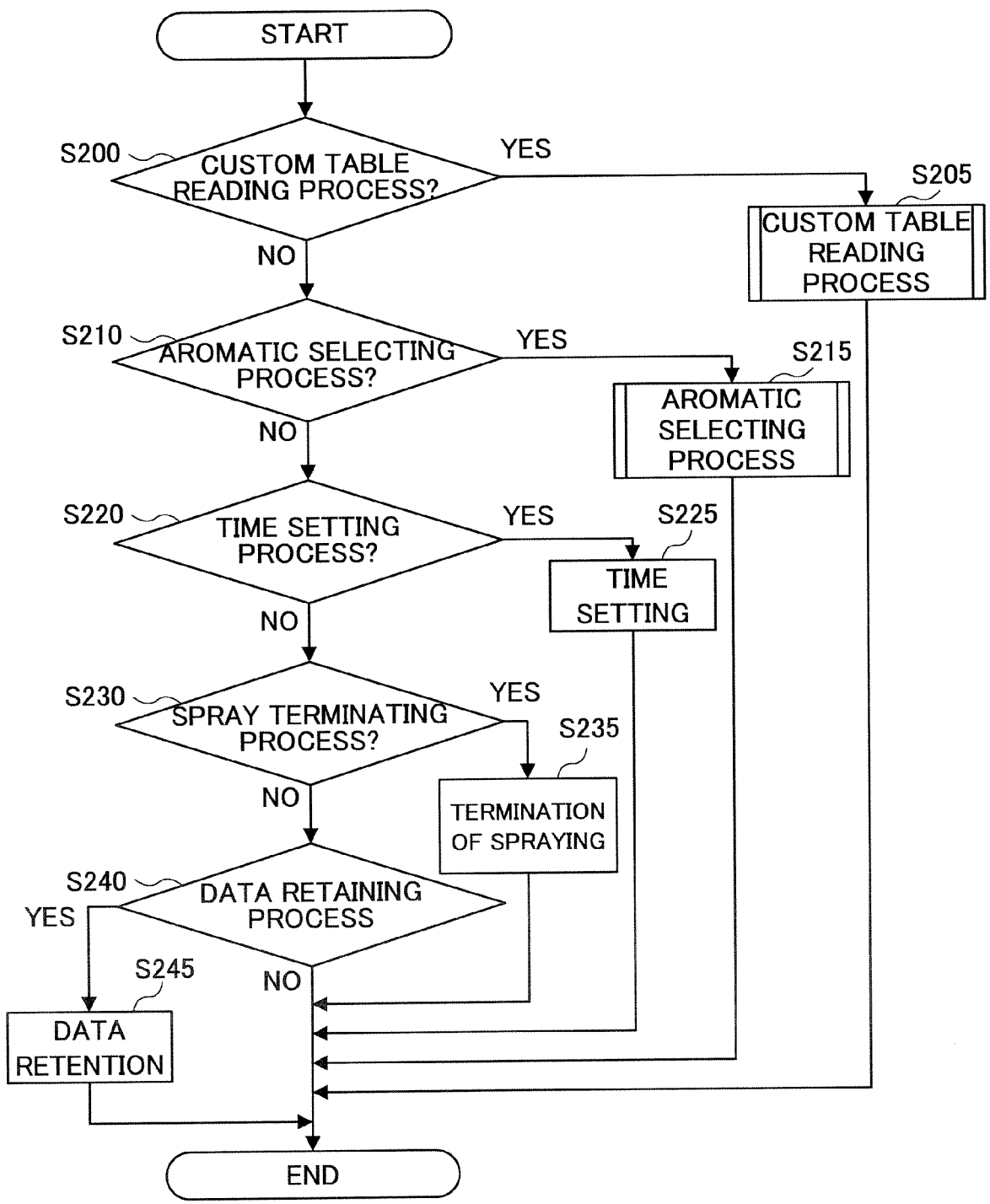

In Step S105, accepting of a selection of an interruption process is started, and thereafter an interruption process is performed at an arbitrary timing. Specifically, for example, a display for accepting a selection from the group consisting of a custom table reading process, an aromatic selecting process, a time setting process, a spray terminating process, and a data retaining process, is presented to accept the user's selection, thereby performing the selected process. The details of the interruption processes will be described later (FIG. 9).

Figure 8:
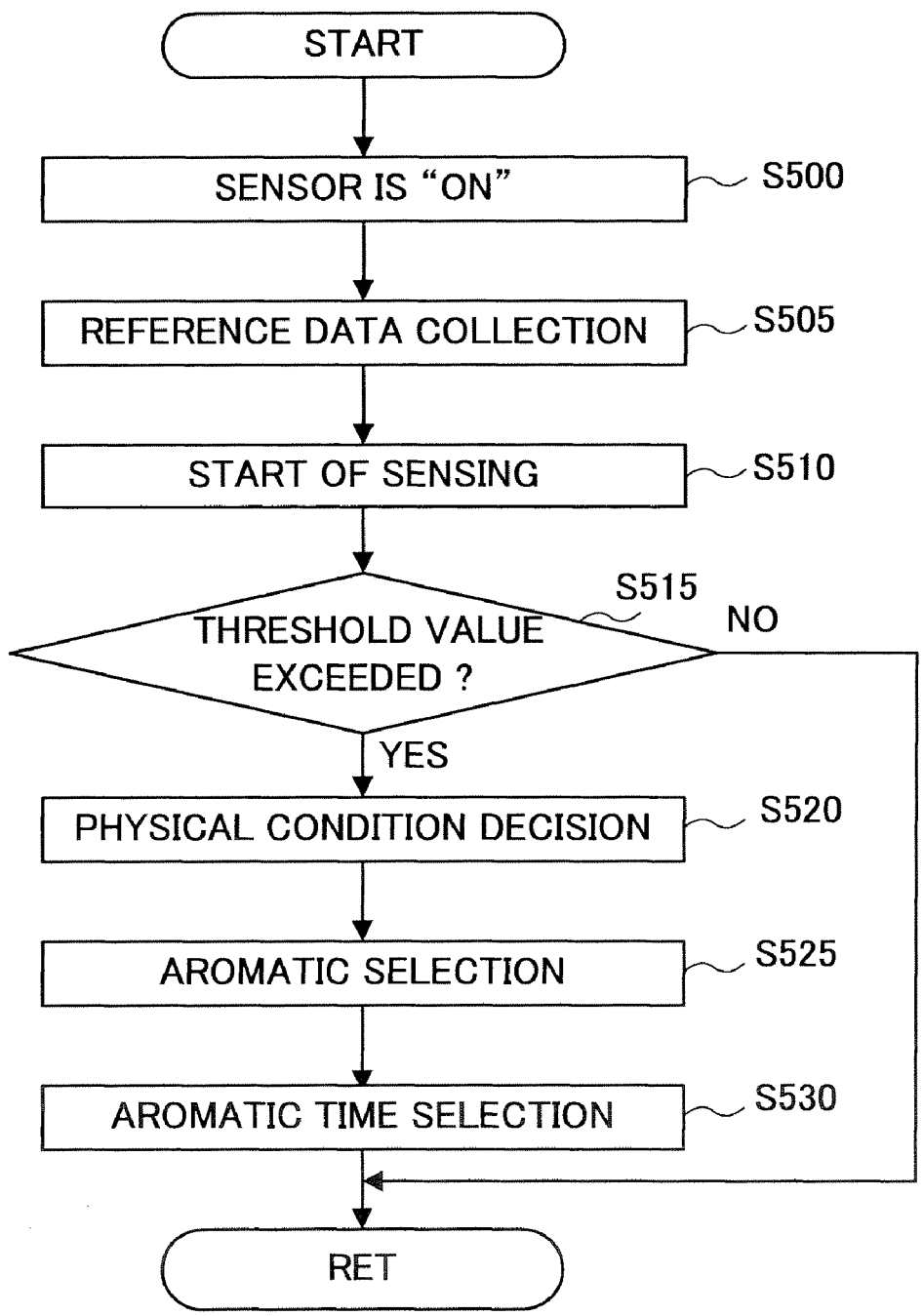

Step S110 is for deciding the temperature of the user's finger or palm by the use of the temperature sensor 310. The details of this process will be described later (FIG. 8). The temperature decision process is for deciding the user's feeling and physical condition based on temperature signals from the temperature sensing parts 30a and 30b, and then selecting an aromatic, a spray time, and a spray interval, which are suitable for stabilizing the user's feeling and physical condition. When this process is terminated, the procedure moves to step S115.

Step S115 is for starting or continuing spraying of the aromatic selected in the process of sensing by the sensor in step S110, or for stopping spraying when aromatics to be selected are not set. In cases where the spray is terminated in step S235 in FIG. 9, to be described later, there is no possibility of resuming the spraying of the same aromatic. Specifically, the CPU 110 sends a control signal to the pressure control circuit 560 so as to feed compressed air from the compressor 510 and spray aromatics from the nozzles 550a, 550b and 550c. In addition, the timer 130 counts the spray time. When this process is terminated, the procedure moves to step S120.

Step S120 is for deciding whether spray time and spray interval have been selected in step S110.

Figure 12:
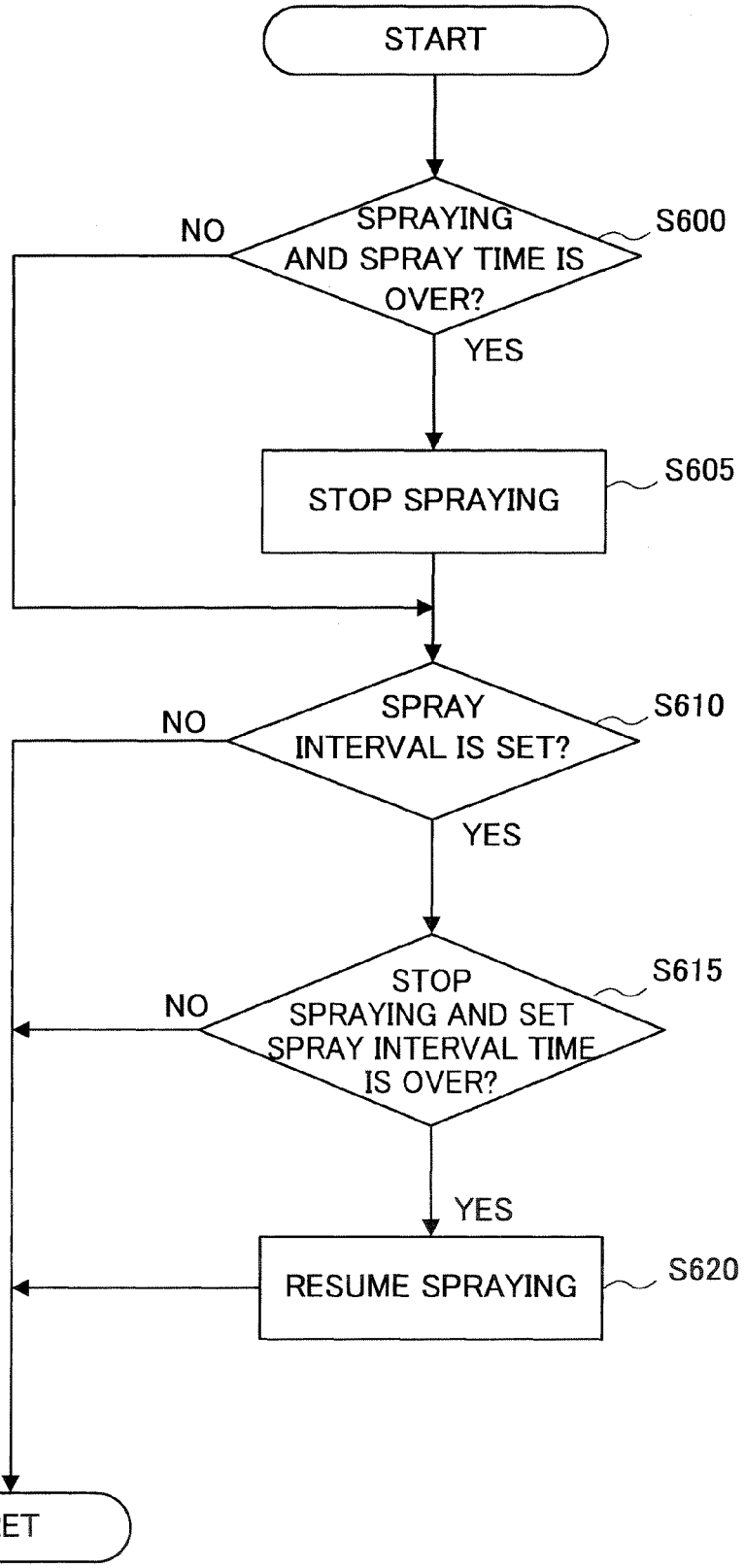

Step S125 is for deciding spray time and spray interval. In this process, it is decided whether or not the spray time has elapsed or whether the spray is performed at the set spray interval, based on the data of the set spray time and the set spray interval. The details of this process will be described later (FIG. 12). When this process is terminated, the procedure moves to step S130.

In step S130, the CPU 110 decides whether the operations of the CPU 110 and the peripheral devices are terminated or not. Specifically, the CPU 110 terminates the operations of the CPU 110 and the peripheral devices by accepting an OFF setting of the power switch. Alternatively, in step S105, the options of terminating the operation may be displayed on the display part 40 so that the operation of the CPU 110 and the operations of the peripheral devices are terminated by accepting a selection from the options. This terminates the main flow. In cases of not accepting the selection of the termination of the operations of the CPU 110 and the peripheral devices, the procedure is returned to step S110 so as to perform again a sensing process A by the sensor.

Sensing Process A by Sensor

A subroutine of the sensing process A by the sensor to be executed in step S110 in FIG. 7 will be described below with reference to FIG. 8.

In step S500, the CPU 110 starts acceptance of a temperature signal from the temperature sensor 310. That is, this process is executed by starting a signal process in the signal processing circuit 320. When this process is terminated, the procedure moves to step S505.

In step S505, the CPU 110 collects reference data. Specifically, it stores in the storage part 120 the temperature signal values of the respective sensors when acceptance of the temperature signal from the temperature sensor 310 is started. Preferably, the temperature signal value at the start is obtained when the user's feeling and physical condition are stable. It is also preferable to employ an average value of the temperature signals values obtained when the user's finger or palm makes contact with the temperature sensor a specified number of times. Alternatively, the storage part 120 may previously store a predetermined temperature signal value as reference signal value data, in order that the CPU 110 reads this reference signal value data from the storage part 120 in step S505. When this process is terminated, the CPU 110 moves the procedure to step S510.

In step S510, the CPU 110 starts to sense the temperature of the user's finger and the like, through the temperature sensor 310. Specifically, the signal processing circuit 320 accepts a real-time temperature signal from the temperature sensor 310, and the CPU 110 starts monitoring of input signals. When this process is terminated, the procedure moves to step S515.

In step S515, the CPU 110 decides whether or not the temperature signal from the temperature sensor 310 exceeds a threshold value. Specifically, for example, the CPU 110 refers to a feeling and physical condition decision table 70 (FIG. 15) stored in the storage part 120, and decides whether or not a variation value relative to the reference signal of the input signals in the respective sensors, or the elapsed time from the start of variations exceeds the value of a threshold value field 702. When the CPU 110 decides that the threshold value has been exceeded, the procedure moves to step S520. When the CPU 110 decides that the threshold value has not exceeded, the sensing process A by the sensor is terminated.

In step S520, the CPU 110 decides the feeling and physical condition. Specifically, for example, the CPU 110 refers to the feeling and physical condition decision table 70 (FIG. 15) stored in the storage part 120, and refers to the type of feeling and physical condition associated, on a physical condition decision field 704, with the threshold value decided in step S515. Thus, the CPU 110 decides this is the user's present feeling and physical condition. When this process is terminated, the procedure moves to step S525.

In step S525, the CPU 110 performs the process of selecting an aromatic for stabilizing the feeling and physical condition decided in step S520. Specifically, for example, the CPU 110 refers to the aromatic selection table 72 (FIG. 16) based on the physical condition decision stored in the storage part 120, and selects from an aromatic field 724 the aromatic associated with the feeling and physical condition decided in step S520. The individual aromatics are associated with the names of tanks each containing the corresponding aromatic. Instead of the aromatic names, the tanks names may be directly associated with the aromatic field. When this process is terminated, the procedure moves to step S530.

In step S530, the CPU 110 performs the process of selecting the spray time and the spray interval of the aromatic selected in step S525. Specifically, for example, it refers to a spray time selection table 74 (FIG. 17) based on the physical condition decision stored in the storage part 120, and selects the time and the interval associated with the type of the feeling and physical condition decided in step S520, from a time field 744 and an interval field 746, respectively. When this process is terminated, the sensing process A by the sensor is terminated.

The process sequence of step S525 and step S530 is arbitrary. The aromatic selection table 72 based on the physical condition decision in FIG. 16, and the spray time selection table 74 based on the physical condition decision in FIG. 17 may be summed up in a single table so as to select the aromatic, spray time, and spray interval by the same process.

As an alternative, without performing the physical condition decision process in step S520, for example, an aromatic spray time selection table 80 (FIG. 19) based on the sensor output values stored in the storage part 120 may be referred to, to select the aromatic, the spray time, and the spray interval associated with the threshold value decided in step S515, from an aromatic field 804, a time field 806, and an interval field 808, respectively.

Interruption Process Flow

The interruption process, which is accepted and started in step S105 in FIG. 7, will be described with reference to FIG. 9.

Steps S200, S210, S220, S230, and S240 are for deciding the kind of interruption process selected by the user. When the selected interruption process is the custom table reading process, the procedure moves to step S205. When the selected interruption process is the aromatic selecting process, the procedure moves to step S215. When the selected interruption process is the time setting process, the procedure moves to step S225. When the selected interruption process is the spray terminating process, the procedure moves to step S235. When the selected interruption process is the data retaining process, the procedure moves to step S245.

Step S205 is for reading in the storage part 120 the various tables previously customized by the user (FIGS. 15 to 20).

Figure 10:
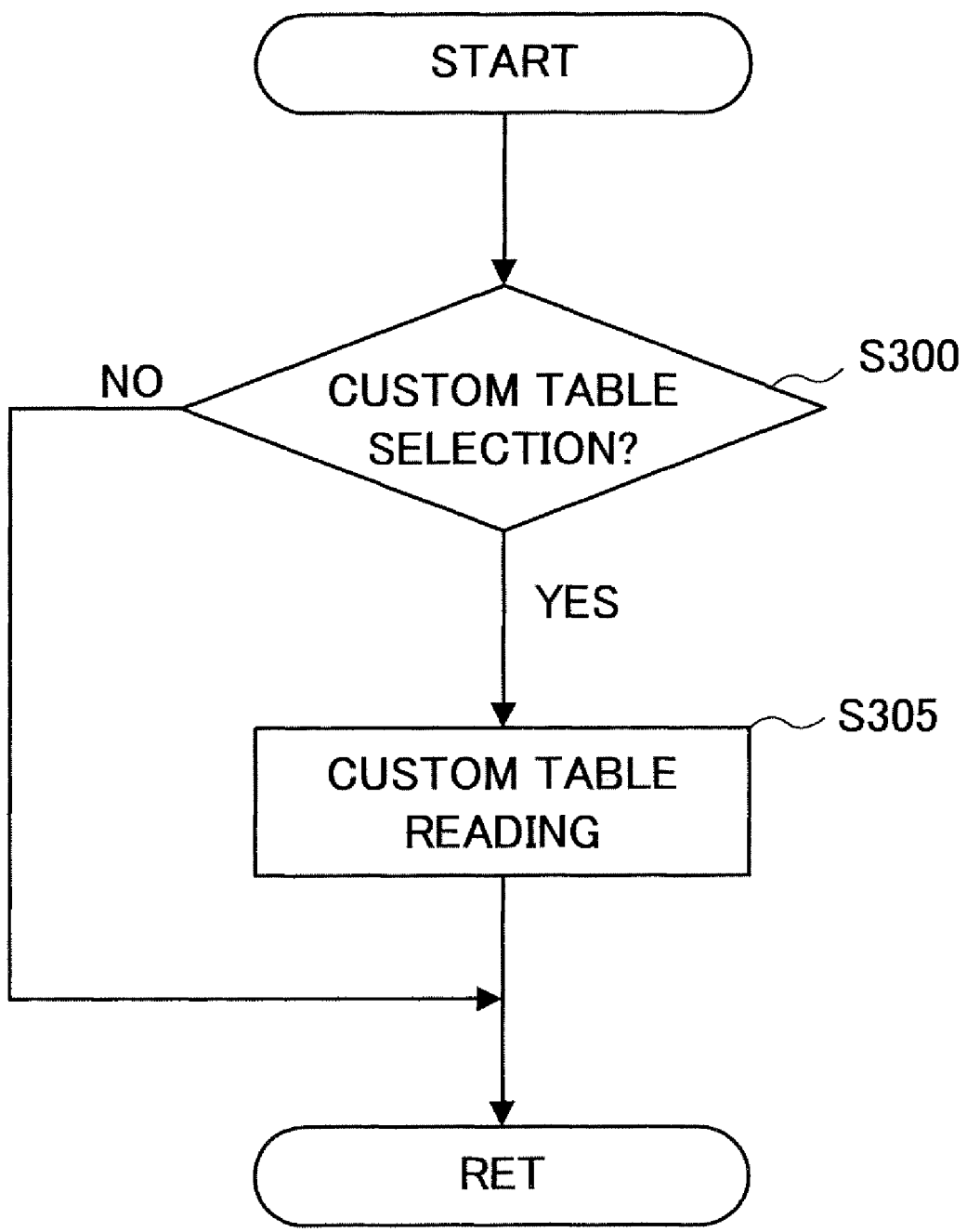

The details of the process will be described later (FIG. 10). When this process is terminated, the CPU 110 terminates the interruption process.

Figure 11:
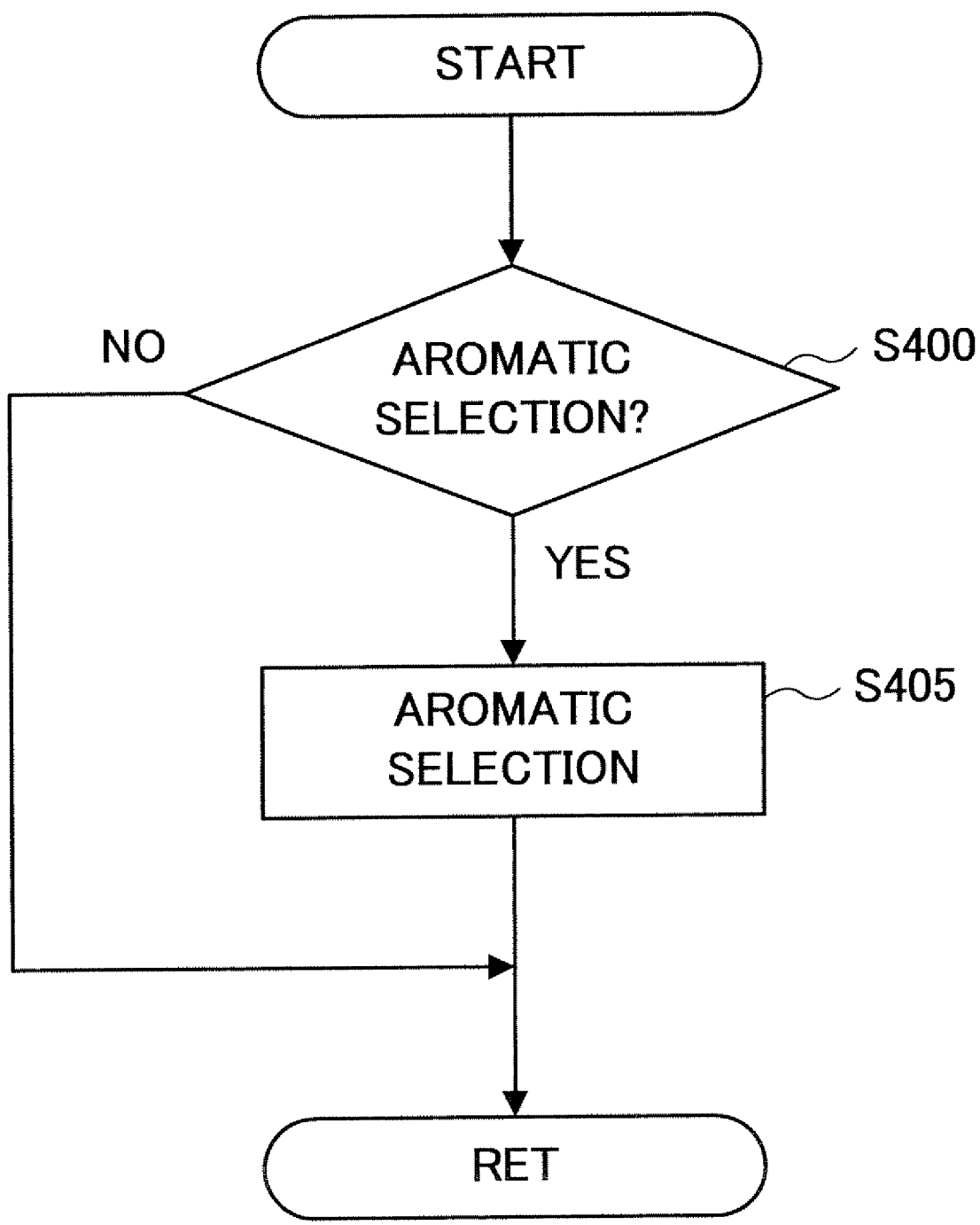

Step S215 is for accepting a selection of an aromatic to be sprayed, based on the user's preference. The details of this process will be described later (FIG. 11). When this process is terminated, the CPU 110 terminates the interruption process.

Figure 23:
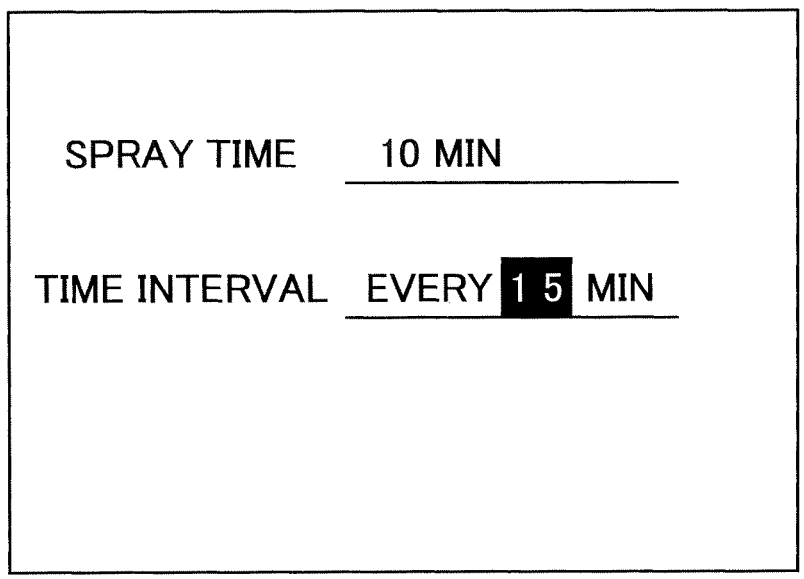
FIG. 23 shows a display during a spray time and spray interval setting process in the information processing unit 1 of an example of the preferred embodiment.

In step S225, the CPU 110 accepts the setting of a spray time or a spray time interval. Specifically, the CPU 110 directs the display part 40 to display a setting screen as shown in FIG. 23. For example, an input box for accepting inputs of a spray time and a spray time interval is displayed, and the inputs are accepted by input means such as a keyboard, a software keyboard, and a touch panel. In the succeeding process to be executed, the time and interval data in the table are to be replaced for use. When this process is terminated, the CPU 110 terminates the interruption process.

Alternatively, in step S225, in order that the whole time and interval data of the spray time selection table 74 based on the physical condition decision, and the aromatic and spray time selection table 80 based on the sensor output values can be changed, a display of a table format (not shown) may be added to the display part 40, so that any arbitrary spray time and spray interval data can be selected and changed.

Step S235 is for terminating the aromatic spray operation. Specifically, if the aromatic spray is continued, the CPU 110 sends a stop signal to the pressure control circuit 560 in order to stop the spraying from the nozzles 550a, 550b, and 550c. When this process is terminated, the CPU 110 terminates the interruption process.

In step S245, the setting table containing the aromatic data or time data or the interval data set in step S215 and step S225 is retained as a custom table. When this process is terminated, the CPU 110 terminates the interruption process. At the next time, when the CPU 110 and the peripheral devices start operation, this customer table is read in step S100 (FIG. 7).

Custom Table Reading Process

A custom table reading process to be executed in step S205 in FIG. 9 will be described with reference to FIG. 10.

Here, the custom table is attained by accepting the change to the specified data requested by the user which was retained in step S245, although it has the same configuration as the setting table of default (Tables 70, 72, 74, 76, 80, and 82 in FIGS. 15 to 20) read in step S100 (FIG. 7). In the custom table reading process, the CPU 110 reads the custom table instead of the setting table of default read in step S100. In the succeeding process to be executed, the data of the custom table is used instead of the setting table of default.

In step S300, the CPU 110 reads the above-mentioned custom table and decides whether the specified data is replaced or not. Specifically, the CPU 110 directs the display part 40 to display a selection screen as shown in FIG. 21. For example, a list of file names storing the custom table is displayed to accept inputs through a pointing device such as a mouse, or input means such as a keyboard and a touch panel. Alternatively, the custom table may be stored in the storage part 120, or in an external storage unit when it is connected.

In step S300, when accepted a selection of a file name is accepted, the CPU 110 moves the procedure to step S305. When a selection of a file name is not accepted, by canceling, or the like, the CPU 110 terminates the custom table reading process.

In step S305, the CPU 110 reads from the storage part 120 the custom table accepted in step S300, and replaces the data of the setting table of default. When this process is terminated, the CPU 110 terminates the custom table reading process.

Alternatively, in the custom table reading process, an ID field may be provided in the tables 70, 72, 74, 76, 80, and 82 so that, by accepting a selection of an ID on the selection screen in step S300, the data of the row corresponding to the ID can be used in the succeeding process to be executed.

Aromatic Selecting Process

An aromatic selecting process to be executed in step S215 in FIG. 9 will be described with reference to FIG. 11.

In step S400, the CPU 110 decides whether an aromatic to be sprayed is selected or not. Specifically, the CPU 110 directs the display part 40 to display a selection screen as shown in FIG. 22. For example, a list of the names of aromatics set to the aromatic tanks 54a, 54b and 54c, or a list of the aromatic tank names, or both lists are displayed to accept inputs through a pointing device such as a mouse, or input means such as a keyboard and a touch panel. Here, the number of aromatics selected for spraying is not limited to one, and selections of a plurality of aromatic names or aromatic tanks names may be accepted simultaneously.

In step S400, if a selection of an aromatic is accepted, the CPU 110 moves the procedure to step S405. If a selection of an aromatic name is not accepted, by canceling or the like, the CPU 110 terminates the aromatic selecting process.

Alternatively, in step S400, in order that the whole aromatic data of the aromatic selection table 72 based on the physical condition decision, and the aromatic and spray time selection table 80 based on the sensor output values can be changed, a display of a table format (not shown) may be added to the display part 40, enabling any arbitrary aromatic data to be selected and changed.

In step S405, the CPU 110 stores the aromatic data accepted in step S400 and employs this instead of the aromatic data, in the tables in the succeeding process to be executed. When this process is terminated, the CPU 110 terminates the aromatic selecting process.

Spray Time and Spray Interval Decision Process

A spray time and spray interval decision process to be executed in step S125 in FIG. 7 will be described with reference to FIG. 12.

In step S600, the CPU 110 decides whether the spray time selected in step S110 (FIG. 7) has elapsed or not. Specifically, it decides whether or not the aromatic is being sprayed presently, and the spray time, whose counting by a timer 130 was started in step S115 (FIG. 7), has passed the spray time selected in the step S110. If is decided that the spraying is stopped, or that it has not yet passed the selected spray time, the CPU 110 moves the procedure to step S610. If it is decided that the spraying is continuing and the selected spray time has elapsed, the CPU 110 moves the procedure to step S605.

In step S605, the CPU 110 stops spraying the aromatic.

In step S610, the CPU 110 decides whether or not there is a setting for a spray interval. Specifically, it decides whether the spray interval setting is selected or not in step S110 (FIG. 7). If there is a spray interval setting, the CPU 110 moves the procedure to step S615. In the absence of a spray interval setting, the CPU 110 terminates the spray time and spray interval decision process.

In step S615, the CPU 110 decides whether the spray interval time has elapsed or not. Specifically, it decides whether or not the spray interval time, whose counting by the timer 130 was started in step S605, has passed the spray interval time selected in the step S110 (FIG. 7). If it is decided that the spraying is continuing, or that the selected spray interval time has not yet been passed, the CPU 110 terminates the spray time and spray interval decision process. If it is decided that the spraying is stopped and the spray interval time has elapsed, the CPU 110 moves the procedure to step S620.

In step S620, the CPU 110 resumes the aromatic spray.

Main Flow B

Figure 13:
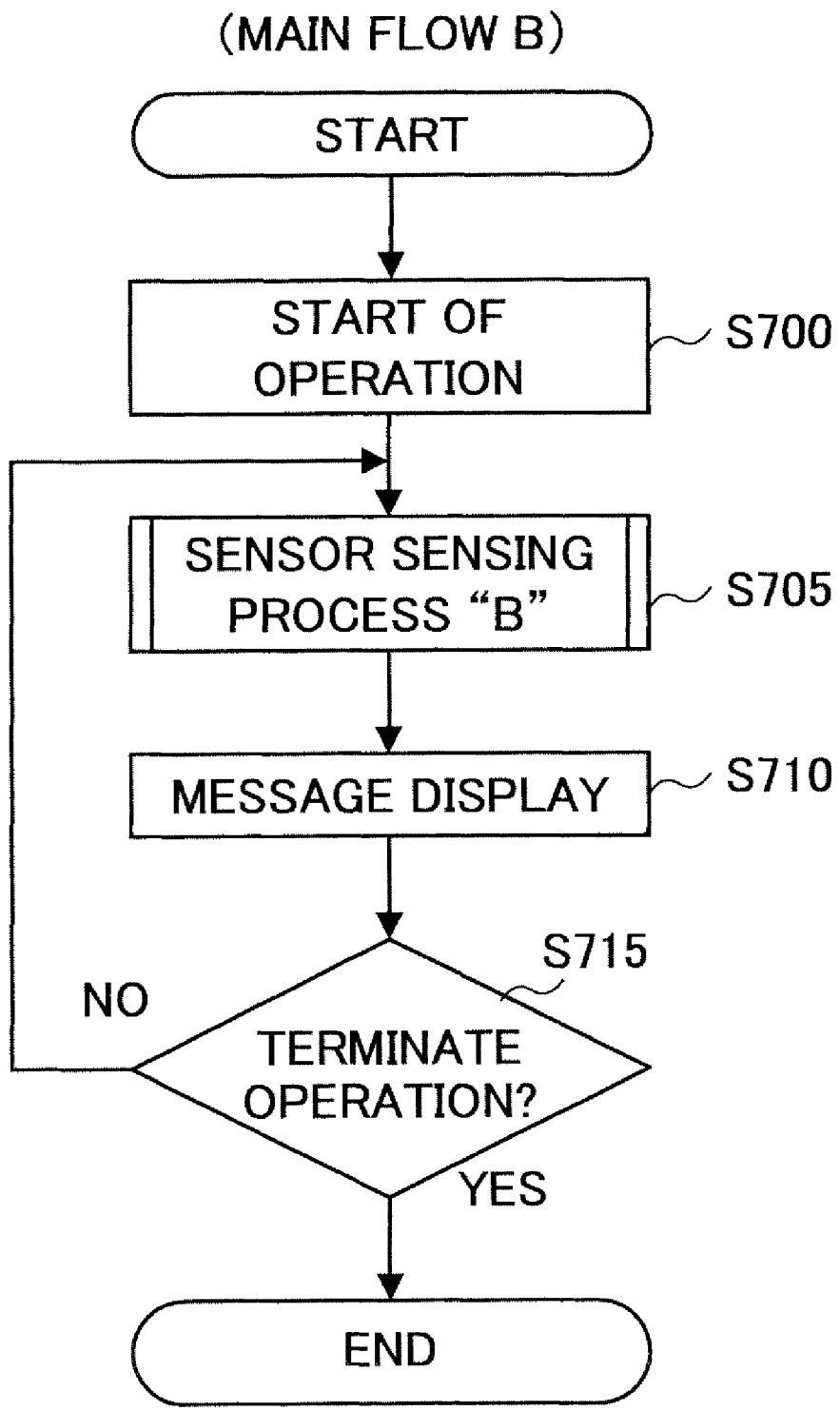

Thus, the main flow A (FIG. 7) performs the aromatic spray for stabilizing the feeling and physical condition. As an alternative to the aromatic spray, a case of displaying a countermeasure message is shown in FIG. 13.

Figure 14:
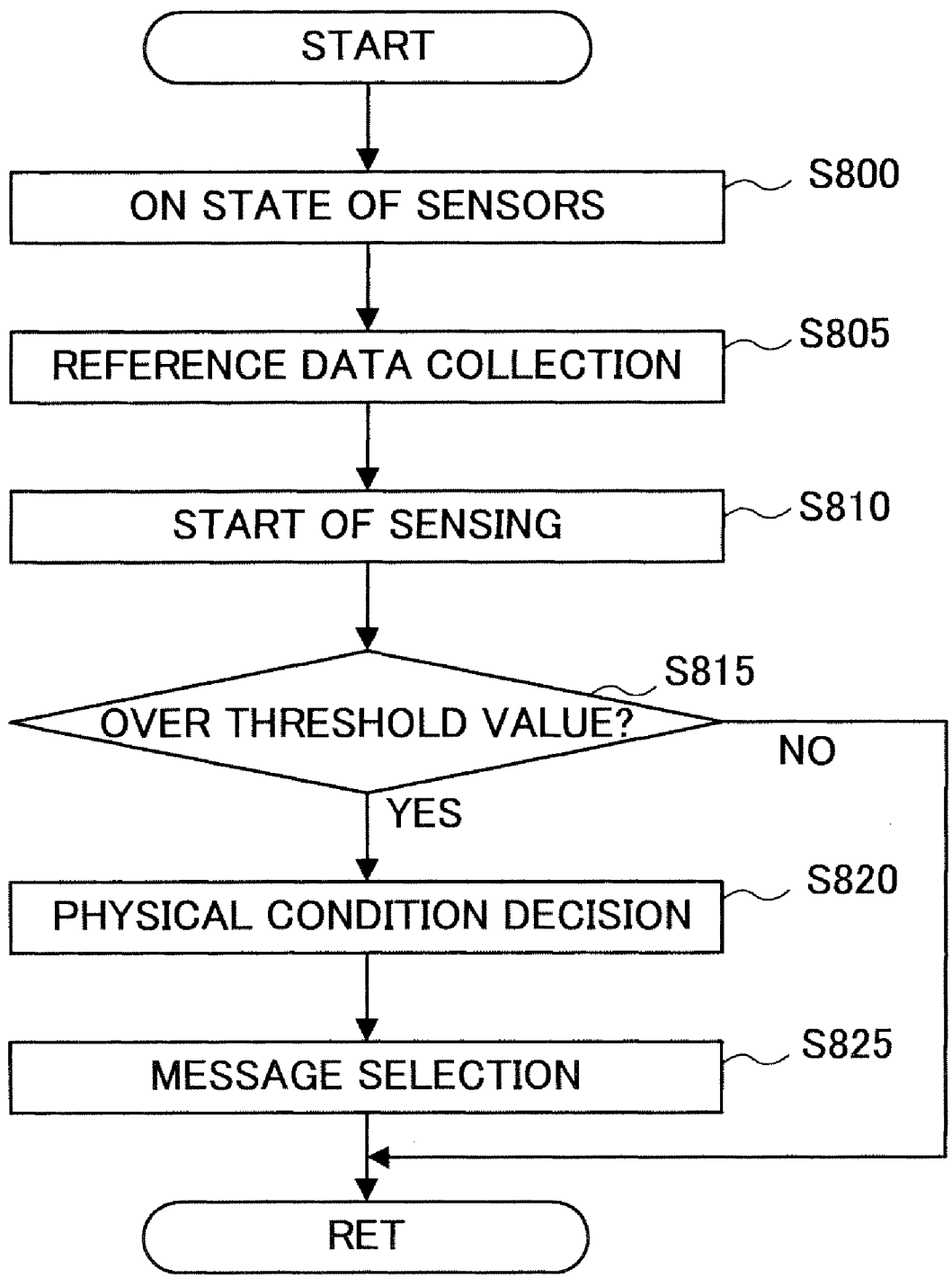

Unlike the sensing process A by the sensor in the main flow A, in a sensing process B of step S705, the CPU 110 selects a countermeasure message instead of selecting an aromatic, a spray time, and a spray interval. The details of this process will be described later (FIG. 14).

Figure 24:
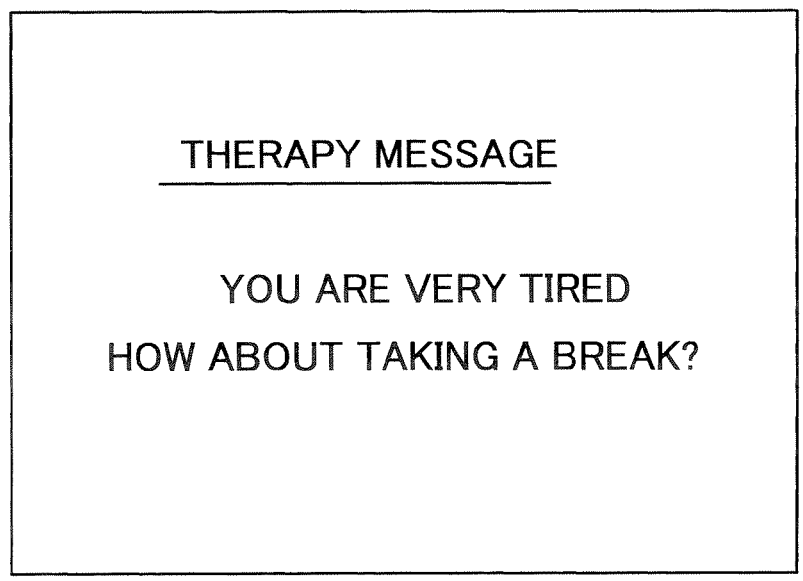
FIG. 24 shows a display of countermeasure messages in the information processing unit 1 in an example of the preferred embodiment.

In step S710, the CPU 110 performs the process of displaying a countermeasure message instead of the aromatic spray process of the main flow A. Specifically, the CPU 110 directs the display part 40 to display the countermeasure message selected in step S705, as shown in FIG. 24.

Sensing Process B

The sensing process A (FIG. 8) is to select an aromatic, a spray time, and a spray interval. Instead of selecting these, the case of selecting a message is shown in FIG. 14.

In step S825, the CPU 110 performs the process of selecting the message corresponding to the kind of feeling and physical condition decided in step S820. Specifically, for example, it refers to the message selection table 76 (FIG. 18) based on the physical condition decision stored in the storage part 120, and selects from the message field 764 the message associated with the kind of the feeling and physical condition decided in step S820.

Alternatively, instead of performing the physical condition decision process of step S820, for example, the message selection table 82 (FIG. 20) based on the sensor output values stored in the storage part 120 may be referred to, to select from a message field 824 the message associated with the threshold value decided in step S815.

Figure 25:
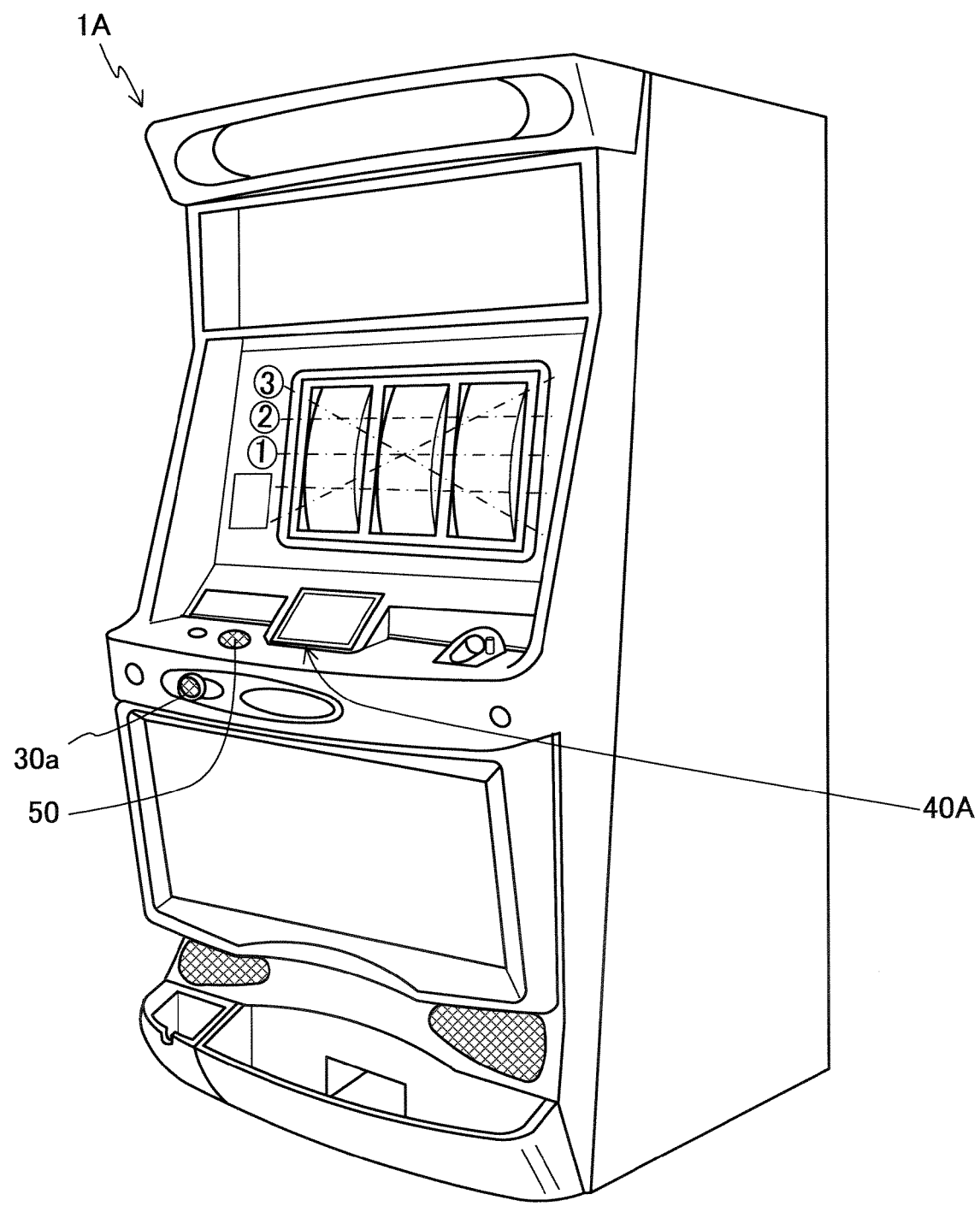
FIG. 25 shows a physically schematic configuration of a game machine 1A according to an example of the preferred embodiment of the present invention.

FIG. 25 shows a case where the above-mentioned information processing unit is applied to a game machine 1A. The game machine 1A may be a slot machine as shown in FIG. 25, or other game machines such as a gaming machine, a pachinko (pinball) machine, a card game machine, and the like. Like the above-mentioned information processing unit 1, the game machine 1A is constructed of an aromatic sprayer 50, input parts (for example, the levers of a slot machine) each containing a temperature sensing part 30*a*, and a display part 40A. These components may be constructed so as to have the same function as the information processing unit 1. The number of the temperature sensing parts 30*a* is not limited to this.

In order to measure the user's body temperature more suitably, it is preferable that the temperature sensing parts 30*a* are provided on the surface of the lever serving as the input part of the game machine 1A, with which the user's finger skin, palm skin, or the like is subjected to frequent contact.

In accordance with the foregoing preferred embodiment, firstly, the information processing unit can measure the user's hand temperature in response to a contact of the user's hand, and spray an aromatic in the mist state, depending on the determination of the user's hand temperature. This enables the user's feeling and physical condition to be stabilized, for example, by aromatherapy effects.

Secondly, the information processing unit can select, from a plurality of different kinds of aromatics, a suitable aromatic depending on the determination of the user's finger temperature. Therefore, the kind of aromatic can be changed and sprayed depending on, for example, the user's finger temperature thus measured.

More particularly, a certain aromatic can be sprayed if the hand temperature falls rapidly, whereas another aromatic can be sprayed if the hand temperature rises rapidly. Alternatively, a plurality of different aromatics may be mixed and sprayed. As a result, the user's feeling and physical condition can be stabilized more suitably by selecting a suitable aromatic, for example.

Thirdly, the aromatic spray part is provided on the outside of the main body of the information processing unit. This enables the aromatic spray part to be provided independently from the main body of the information processing unit. Hence, the user can put the aromatic spray part at a suitable position so that an aromatic can be sprayed more suitably. As a result, the aromatic spray part can be put on, for example, a desk near the user's nose, with the main body placed below the desk.

Fourthly, the information processing unit can display a countermeasure message on the display part, depending on the user's hand temperature. Consequently, depending on the user's hand temperature, it is possible to display, for example, a message advising the user to take a break or have a meal. As a result, the user can maintain his/her feeling and physical condition by taking measures according to the countermeasure message.

Fifthly, the information processing unit has the temperature sensor in a mouse or a keyboard. Hence, in response to the user's contact with the mouse or the keyboard, the user's hand temperature can be sensed, thus leading to the same effects as stated in the foregoing first to fourth effects.

Sixthly, the game machine is adapted to measure the user's hand temperature in response to contact of the user's hand, and spray an aromatic in a mist state depending on the determination of the user's hand temperature. This enables the user's feeling and physical condition to be stabilized, for example, by aromatherapy effects.

Thus, the preferred embodiment of the present invention provides the information processing unit which can automatically select an aromatic for stabilizing and change in the user's feeling and physical condition change, and spray it to a suitable location depending on the user's hand temperature, or which can display a countermeasure message for maintaining the physical condition. This positively stabilizes the user's feeling and physical condition.

While preferred embodiments of the present invention have been described and illustrated above, it is to be understood that they are exemplary of the invention and are not to be considered to be limiting. Additions, omissions, substitutions, and other modifications can be made thereto without departing from the spirit or scope of the present invention. Accordingly, the invention is not to be considered to be limited by the foregoing description and is only limited by the scope of the appended claims.

What is claimed:

1. An information processing unit comprising:
    an input part with a temperature sensor which accepts an input operation of a user and, in response to a contact of the user's hand at time of input, measures the temperature of the hand;
    a container for holding an aromatic;
    an aromatic spray part having a passage communicating with the container and a nozzle communicating with the passage; and
    an aromatic spray controller that is connected via an interface to the temperature sensor and controls the aromatic spray part, based on a temperature signal received from the temperature sensor, wherein, the aromatic spray controller receives the temperature signal measured by the temperature sensor and, when a temperature indicated by the temperature signal reaches a predetermined temperature, outputs to the aromatic spray part an aromatic spray start signal to execute an aromatic spray from the nozzle of the aromatic spray part.

2. The information processing unit according to claim 1, wherein,
the container of the aromatic spray part is constructed so that a plurality of different kinds of aromatics can be held,
a plurality of nozzles is provided so that different aromatics can be sprayed, and
the aromatic spray controller, depending on the temperature signal received from the temperature sensor, outputs to the aromatic spray part an aromatic spray start signal to execute a suitable kind of aromatic spray.

3. The information processing unit according to claim 1, wherein the aromatic spray part is provided outside of a main body of the information processing unit.

4. The information processing unit according to claim 1, wherein the input part is a mouse or a keyboard.

5. The information processing unit according to claim 1, wherein the nozzle of the aromatic spray part is provided either inside the main body of the information processing unit or inside the input part, or alternatively, either outside the main body of the information processing unit or outside the input part.

6. A game machine comprising:
an input part with a temperature sensor which accepts an input operation of a user and, in response to a contact of the user's hand at time of input, measures the temperature of the hand;
a container for holding an aromatic;
an aromatic spray part having a passage communicating with the container and a nozzle communicating with the passage; and
an aromatic spray controller that is connected via an interface to the temperature sensor and controls the aromatic spray part, based on a temperature signal received from the temperature sensor, wherein,
the aromatic spray controller receives the temperature signal from the temperature sensor and, when a temperature indicated by the temperature signal reaches a predetermined temperature, outputs to the aromatic spray part an aromatic spray start signal to execute an aromatic spray from the nozzle of the aromatic spray part.

7. The game machine according to claim 6, wherein,
the container of the aromatic spray part is constructed so that a plurality of different kinds of aromatics can be held,
a plurality of nozzles is provided so that different aromatics can be sprayed, and
the aromatic spray controller, depending on the temperature signal received from the temperature sensor, outputs to the aromatic spray part an aromatic spray start signal to execute a suitable kind of aromatic spray.

8. The game machine according to claim 6, wherein the aromatic spray part is provided outside of a main body of the game machine.

9. The game machine according to claim 6, wherein the nozzle of the aromatic spray part is provided either inside the main body of the game machine or inside the input part, or alternatively, either outside the main body of the game machine or outside the input part.

* * * * *